United States Patent [19]

Sohn et al.

[11] Patent Number: 4,865,714
[45] Date of Patent: Sep. 12, 1989

[54] ELECTROPHORETIC GEL COOLED CELL

[75] Inventors: Chul H. Sohn, Irvine; Cynthia R. Blessum, Pedley; Steven C. Gage, Brea, all of Calif.

[73] Assignee: Beckman Instruments, Inc., Fullerton, Calif.

[21] Appl. No.: 74,743

[22] Filed: Jul. 17, 1987

[51] Int. Cl.[4] .................... G01N 27/28; G01N 27/26
[52] U.S. Cl. ........................ 204/299 R; 204/182.8
[58] Field of Search .................... 204/299 R, 182.8

[56] References Cited

U.S. PATENT DOCUMENTS

| | | | |
|---|---|---|---|
| 3,798,152 | 3/1974 | Cawley | 204/299 R |
| 3,829,375 | 8/1974 | Cawley | 204/182.8 X |
| 3,902,987 | 9/1975 | Cawley | 204/299 R |
| 3,932,263 | 1/1976 | Brefka | 204/299 R |
| 3,947,345 | 3/1976 | Grandine et al. | 204/299 R |

OTHER PUBLICATIONS

Instruction Sheet for Corning Temperature-Controlled Cassette Electrophoresis Cell.
American Scientific Products 1987-88 General Catalog, p. 742.

Primary Examiner—John F. Niebling
Assistant Examiner—John S. Starsiak, Jr.
Attorney, Agent, or Firm—William H. May; Gary T. Hampson

[57] ABSTRACT

An electrophoretic gel cooled cell including a gel supporting surface. The cell includes members for holding gels against the supporting surface such that gels of either of two dimensions may be used with the cell. A reservoir adapted to hold a cooling medium shares a common wall with the supporting surface to cool the gel retained by the members. The reservoir has a large opening which may be closed by a cover for easy insertion and removal of the cooling medium from the reservoir. A venting valve in the reservoir cover vents gas in the reservoir to atmosphere and closes when the cover is in an inverted position to prevent condensate leakage through the vent.

17 Claims, 3 Drawing Sheets

ELECTROPHORETIC GEL COOLED CELL

FIELD OF THE INVENTION

The present invention relates to the field of electrophoresis and more particularly to holders and cells for use with electrophoretic gels.

BACKGROUND OF THE INVENTION

Electrophoresis generally involves the placing of a sample substance, such as blood serum or urine, in a support medium. An electric potential is applied across the medium via electrodes, causing colloidal particles in the sample substance to migrate toward one or the other of the electrodes. The rate of migration is determined in part by the electrical charges on the particles in the sample substance, the composition of the support medium, and the magnitude of the imposed electrical potential. Particles with similar properties tend to separate into defined areas or bands on the support medium and thus a determination can be made as to the amount of each class of particles present in the sample. A graph or analog curve of the relative densities of these areas or bands can provide information as to the relative proportions of each which are contained in the sample substance. Such electrophoretograms provide important information as to blood serum, urine, cerebrospinal fluid, or other biological fluid composition which may be used by clinical pathologists or the like to assess a patient's condition.

A technique has been recently developed that provides improved separation of the sample substance on the medium. This technique, often known as high resolution electrophoresis (HRE), uses an agarose medium or gel and a modified buffer containing calcium ions. The HRE technique also employs relatively higher electric potentials across the gel than conventional electrophoretic techniques.

A difficulty with HRE, however, is that the higher voltage causes heating in the gel. If sufficient heat is generated, the gel and the resulting electrophoretogram may be damaged or destroyed. To overcome medium heating, it is known to cool the gel while the higher voltage is applied. For example, a cooled electrophoresis cell is available from Corning Medical, Corning Glass Works, Palo Alto, Calif. The Corning cell includes a gel holder which shares a common wall with a tank into which ice, a cooling liquid or a liquid/ice slurry may be placed. The holder retains the gel such that a portion of the gel is pressed against the common wall.

The Corning cell, however, has several drawbacks. For example, the common wall is significantly shorter than the gel along the direction that the electric current is applied. Thus a relatively limited portion of the gel is actually held against the common wall where maximum cooling can take place. Furthermore, the gel holder can accept only a single sized gel in the direction that electric current is applied. Lastly, the tank includes a small access hole that makes it difficult to fill or empty the tank.

Thus there is a need for a cooled cell that overcomes the limitations of the Corning cell, providing a conveniently used, efficient cooled cell for use in electrophoresis.

SUMMARY OF THE INVENTION

The present invention overcomes the limitations noted above. The cooled cell of the present invention is convenient to use, allowing easy handling of a cooling medium. Uniquely, the cell can hold gels of two different lengths. This is a particular advantage where the cell is used with a rectangular electrophoresis gel having edge dimensions sized to correspond to the two different lengths. Such a rectangular gel can thus be held in place by either of two sets of opposite edges, allowing the gel to be electrophoresed along either the gel's shorter or longer dimension.

A cooled cell in accordance with the present invention includes a gel holder, a base and a cover. The gel holder may include members having protrusions adapted to engage opposite side edges of a gel. The first set of protrusions are spaced so as to hold a gel having a first length. The members also include a second set of protrusions differently spaced as compared to the first set and adapted to engage opposite edges of a gel. The second set of protrusions are spaced so as to hold a gel having a second length. Thus, either gels of different dimensions or, advantageously, a rectangular gel may be used along either a first shorter dimension or along a second longer dimension.

The side walls of the gel holder are formed to define a reservoir and the cell may further include a cover for closing the reservoir. With the cover removed, the reservoir can be easily and quickly filled and emptied. A wall bridging the first and second members forms a gel receiving surface for a gel installed on the holder, enabling heat transfer between the gel and the reservoir.

The cover may include a valve adapted to open when the cell is in place over the reservoir. The cover may be removed and, when turned over to an inverted position, the valve closes to prevent condensate from emptying from the interior surface of the cover onto, for example, a working surface or a user's hand.

DETAILED DESCRIPTION OF THE INVENTION

Figure 1:
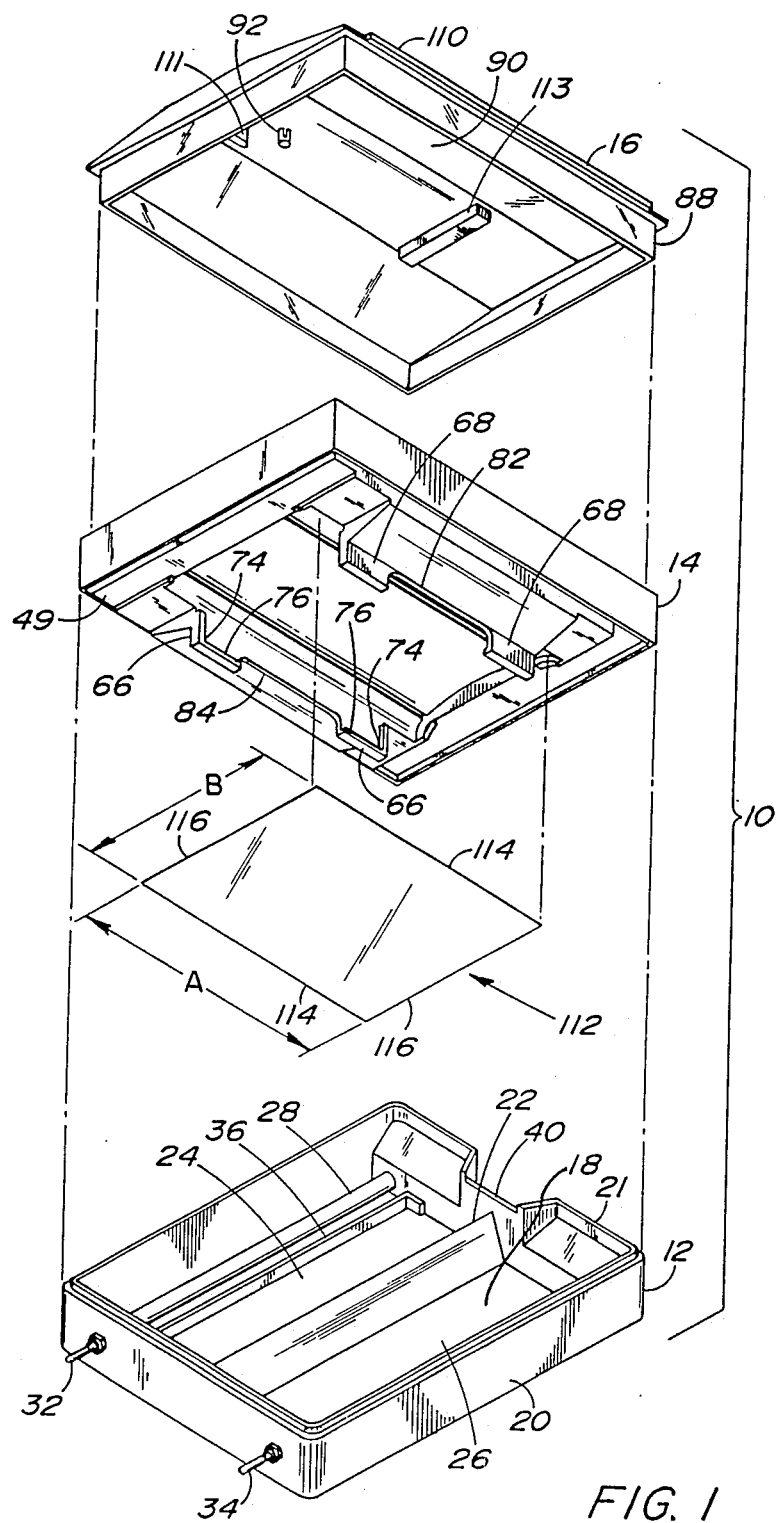
FIG. 1 is an exploded perspective view of a cooled cell in accordance with the present invention.
Figure 2:
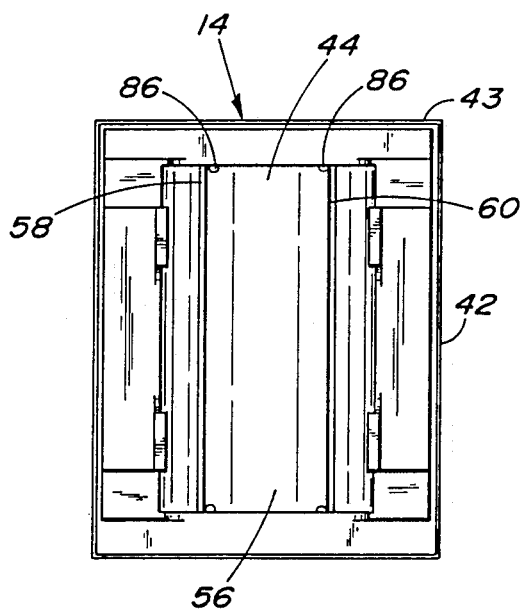
FIG. 2 is a bottom view of a gel holder used in the cell of FIG. 1.
Figure 3:
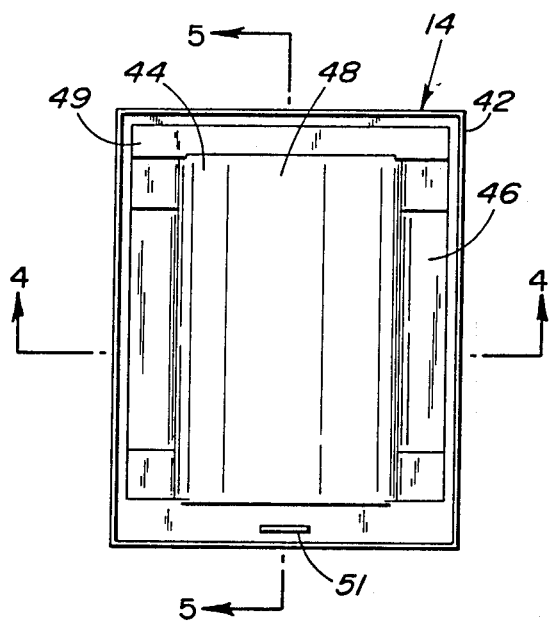
FIG. 3 is a top view of the gel holder of FIG. 2.

With reference to FIG. 1, a cooled cell 10 in accordance with the present invention includes a base 12, gel holder 14, and cover 16. The base 12 is in the form of a low rectangular tray having a bottom 18 and vertical side walls 20. The vertical side walls include a raised lip 21. A raised divider 22 divides the base 12 along its longer dimension into two separate fluid reservoirs 24 and 26. Two electrodes 28 and 30 (FIGS. 1 and 6) are disposed within the reservoirs 24 and 26, respectively. Each of the electrodes 28 and 30 is proximate the side walls 20 and parallel to the divider 22. The electrodes 28 and 30 are connected through the side walls 20 to respective electrical connectors 32 and 34, each of which is suitable for connection to a source of electric potential in an otherwise conventional fashion. Low ridges 36 and 38 formed integrally with the bottom 18 are proximate and parallel to the respective electrodes 28 and 30.

An indentation 40 is formed in the end of the base 12 opposite to that through which the connectors 32 and 34 pass. The indentation 40 provides a convenient means for grasping the assembled cell 10, aids in separating the base 12 from the gel holder 14, and provides a means for determining the orientation of the base 12 with respect to the gel holder 14 such that correct electrical polarity is maintained when the cell 10 is assembled.

Figure 4:
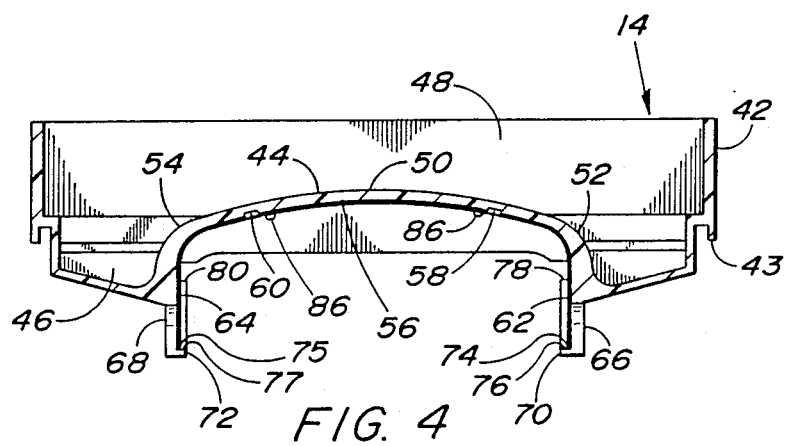
FIG. 4 is a section view of the gel holder taken along line 4—4 of FIG. 3.
Figure 5:
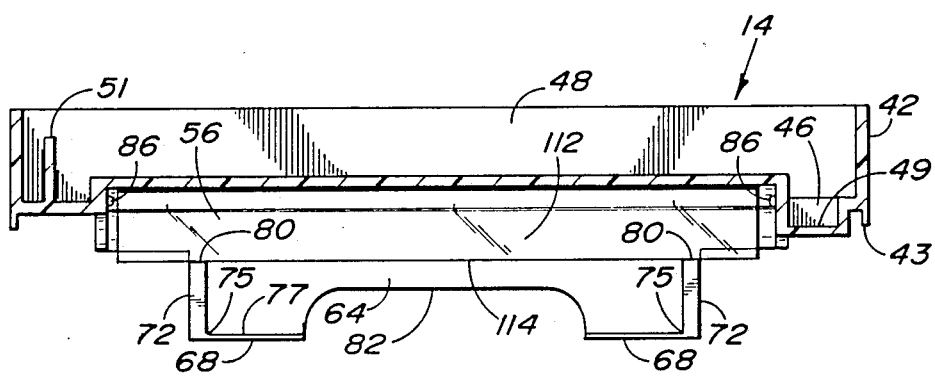
FIG. 5 is a section view of the gel holder taken along line 5—5 of FIG. 3.
Figure 6:
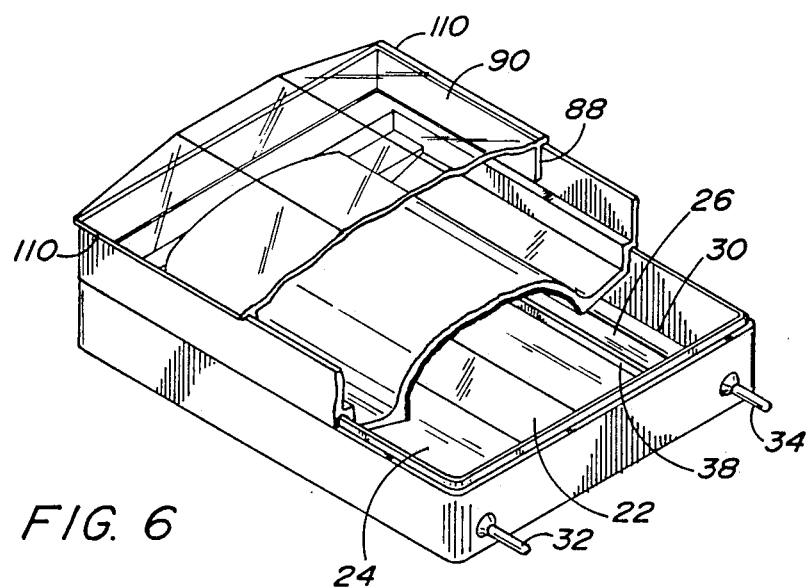
FIG. 6 is a assembled perspective view of the cooled cell of FIG. 1.

With reference now particularly to FIGS. 2-5, the gel holder 14 includes a peripheral side wall 42 having a depending lip 43 adapted to engage the lip 21 of the base 12. The bottom of the holder 14 comprises a central curved heat transfer wall 44 and a trough 46 formed around the periphery of the wall 44. Together, the side wall 42, heat transfer wall 44 and trough 46 form a liquid reservoir 48 adapted to receive and hold cooling liquid, ice, or a slurry of liquid and ice. A portion 49 of the trough 46 proximate the connectors 32, 34 when the cell is assembled as shown in FIG. 6 is sized to extend below the extension of the lip 43 (FIG. 5). A rib 51 extends upwardly (as viewed in FIG. 5) from the opposite end of the trough 46.

The heat transfer wall 44 comprises a slightly curved central portion 50 and side portions 52 and 54 of pronounced curvature. The side portions 52, 54 and central portion 50 define a gel receiving surface 56 on the lower surface of the wall 44, that is, the surface or side of the wall 44 proximate the base 12 when the cell is assembled as shown in FIG. 6. With the gel holder 14 oriented horizontally as illustrated in FIGS. 4 and 5, the surface 56 curves from an essentially vertical orientation formed by the side portions 52, 54 to a gradually arcing orientation defined by the curved central portion 50. In the embodiment disclosed herein and with gels of the type disclosed herein, the curved central portion 50 is defined by a four inch radius and the side portions 52, 54 are each defined by a 0.32 inch radius. A pair of grooves 58, 60 are formed into the surface 56 and parallel to the longitudinal axis of the surface 56.

Two gel retaining means or members 62 and 64 are disposed on either side of the gel receiving surface 56. The members 62, 64 are parallel to the longitudinal axis of the surface 56 and thus parallel to the grooves 58, 60. Each of the members 62, 64 includes a pair of depending portions 66, 68 at the respective ends of the members 62, 64. Protrusions 70, 72, project from the members 62, 64 and depending portions 66, 68. The protrusions 70, 72 define internal corners 74, 75, edges 76, 77 and edges 78, 80 used to retain gels of either of two different lengths or dimensions as described below. The depending portions 66, 68 define finger access notches 82, 84 for easy gel removal. The gel receiving surface 56 also includes four locating ribs 86 proximate the ends of the surface 56 and the ends of the grooves 58, 60.

In the embodiment disclosed herein, the wall 44 thickness is about 0.060 inch. The gel holder 14 is formed as a unitary structure from ABS plastic. It has been found that ABS plastic exhibits good thermal characteristics, providing heat transfer through the wall 44.

Figure 7:
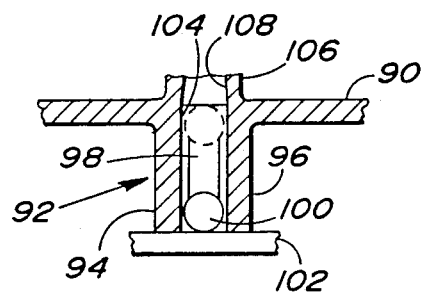
FIG. 7 is a cross-section view of a vent valve useful in the cover of the cell of FIG. 1.

With reference to FIGS. 1, 6 and 7, the cover 16 comprises a depending side wall 88 and a top 90. The side wall 88 is sized to be received within the side wall 42 of the gel holder 14. A vent valve 92 is formed into the top 90. The vent valve 92 includes two depending slightly curved portions 94, 96 (FIG. 7) together defining two slits 98 (only one of which is shown in FIG. 7). A ball 100 is freely retained within the portions 94, 96 by means of a retainer 102 fixed to the ends of the portions 94, 96. A tapered passageway 104 is formed through the top 90 and a boss 106. The raised boss 106 defines a circular opening 108 in the top 90.

The cover 16 may also include projections 110 along the outer upper edges of the cover 16 and parallel with the longitudinal axis of the cover 16 to ease grasping and removal of the cover 16. A rib 111 at the end of the cover 16 proximate the connectors 32 and 34 cooperates with the rib 51 to position the cover 16 as shown. A magnet 113 disposed under the top 90 of the cover 16 is adapted to operate a magnetic switch (not shown) to apply power to the cell 10 in an otherwise conventional fashion.

The cell 10 is adapted to receive and hold an electrophoretic gel 112. The gel 112 is formed from a sheet of a thin, clear flexible material such as polyester or polycarbonate and is coated on one side with a suitable gel material such as agarose. The gel is rectangular is shape having a first longer dimension A parallel to edges 114 and a second shorter dimension B parallel to edges 116. In the embodiment disclosed herein, the gel 112 dimensions A and B are four inches and three inches, respectively. The gel may similar to gels found in a Paragon ® electrophoresis kit, part number 446111, available from Beckman Instruments Inc., Brea, Calif., although other suitable gels will be apparent to those skilled in the art. Advantageously, the gel 112 may be particularly suitable for use in practicing the HRE technique.

In use, the reservoirs 24 and 26 are filled with suitable buffer solutions. The gel 112 first prepared and sample is applied thereto. The gel is the formed to press against the surface 56 with the gel coated surface away from the surface 56. The edges 114 are slipped over and retained by the edges 78 and 80 (as illustrated with respect to edges 80 in FIG. 5) to thereby securely press the gel 112 against the gel receiving surface 56. The ribs 86 prevent the gel edges 116 from resting against either end of the surface 56. The curvatures of the central portion 50 and side portions 52 and 54 match the curvature of the gel 112, thus conforming to the gell 112 and allowing the gel 112 to press firmly against the gel receiving surface 56 for good thermal contact over the gel, preventing hot spots that might otherwise develop. Suitable wicking material such as filter paper (not shown) may be attached to the edges 114 to allow the gel 112 to be electrically connected to the buffer solutions held in the reservoirs 24 and 26. With the gel 112 installed in this fashion, the electrophoretic separation will occur along the shorter dimension B.

The gel holder 14 is assembled to the base 12. The portion 49 will not fit over the indentation 40 and thus the holder 14 must be assembled with the portion 49 proximate the connectors 32 and 34 as illustrated in the Figures, thereby maintaining correct polarity for the gel 112.

Advantageously, with the cover 16 removed the reservoir 48 may be very easily accessed to enable a cooling medium such as a cooling liquid, ice or a liquid and ice slurry to be placed in the reservoir 48. The cover 16 is then placed over the gel holder 14. As so positioned, the ball 100 opens the passageway 104 and opening 108, allowing gas to flow therethrough to prevent a differential pressure from developing between the reservoir 48 and the surrounding environment.

With the cooling medium in place and cover 16 in place, the cell 10 may be connected to an electric potential to perform the HRE technique. Heat generated by the gel 112 in response to the application of a high voltage potential thereto is carried through the heat transfer wall 44, cooling the gel 112 and preventing heat damage thereto. Advantageously, the gel receiving surface 56 provides a large contact surface area as compared to the area of the ge. 112, thereby providing rapid and thorough heat transfer to the cooling medium.

Once the HRE technique has been completed, the cell 10 is disassembled by removing the cover 16 from the holder 14 and the holder 14 from the base 12. With the cover 16 removed and if it is inverted, the ball 100 drops into the tapered passageway 104, closing the passageway 104. The closed passageway 104 prevents condensate formed on the cover 16 during electrophoresing of the gel 112 from flowing, for example, onto a work surface or into the hand of the user. The gel 112 is removed from the holder 14 and analyzed in a conventional fashion.

As a further advantage the gel 112 may be retained in the gel holder 14 with the edges 116 disposed in the buffer solutions contained in the reservoirs 24 and 26. To do so, the gel 112 is first prepared and then formed against the surface 56. Again, the curvature of the portions 50, 52 and 54 conform to the gel 112, promoting intimate contact between the gel 112 and the surface 56 for good thermal contact. The edges 116 are retained by the edges 76, 77 with the corners of the gel 112 in the corners 74, 75 as illustrated in FIG. 4. The cell 10 is assembled as before, the reservoir 48 again providing cooling to the gel 112 as it is electrophoresed. Because the gel 112 is retained with the longer dimension A between the electrodes 28 and 30, electrophoretic separating occurs along dimension A and the resolution of the electrophoresis technique is further enhanced.

It is to be recognized that the same gel 112 need not be used with the cell 0. For example, a family of gels all sized as the gel 112 can be used with the cell 10, some gels used along the dimension A and some along the dimension B, depending upon the composition of the gel and the type of electrophoretic separation sought. With such a family of gels, gel manufacturing cost can be reduced due to the use of a standard gel size. Alternatively, a gel need not be sized to fit into the holder 14 along both gel dimensions.

Another important feature of gels sized as the gel 112 is that two dimensional electrophoretic analyses may be accomplished with the same gel holder 14. For example, a rectangular gel would first be electrophoresed along the dimension A and then turned and electrophoresed along the dimension B. In this fashion, a two dimensional electrophoretic separation is achieved with a single gel holder 14, reducing equipment costs and procedure complexity.

Thus, the cell 10 of the present invention enables gels to be retained so as to enable electrical potential to be applied to gels of two different dimensions, increasing the adaptability of the cel 10. Furthermore, rectangular gels having dimensions particularly adapted to the cell 10 can be used along either, or both, of the gel's two dimensions, thus increasing the utility of the cell 10 and the rectangular gels such as the gel 112. Furthermore, the cell 10 provides easy insertion and removal of cooling medium therefrom. The cell 10 allows venting of the reservoir 48 during electrophoresing but prevents inconvenient draining of condensate when the cover 16 is inverted. These advantages, alone and together, provide a significant advance in the ease and convenience of use of a HRE cell, all important aspects not heretofore available in the HRE art.

It is to be recognized that the present invention is not to be limited to the specific embodiment disclosed herein, but is instead defined by the full scope of the appended claims and all equivalents thereto.

What is claimed is:

1. A device selectively and operatively for use with one of a plurality of electrophoretic gels wherein one such gel has opposite edges defining a first dimension and another such gel has opposite edges defining a second dimension, comprising:
   a gel supporting surface;
   members first means adapted to engage the opposite edges of the one such gel and hold the gel against the gel supporting surface;
   the members including second means adapted to engage opposite edges of the another such gel and hold the gel against the gel supporting surface, and wherein either the first means or the second means is operative at a time.

2. A device as in claim 1 wherein the device further includes a liquid holding reservoir and the gel supporting surface shares a wall that is common with the reservoir.

3. A device as in claim 2 wherein the device further includes a cover adapted to close the reservoir and the cover includes valve means for venting the reservoir when the cover is in a first orientation and for closing when the cover is in a second orientation.

4. A device as in claim 1 wherein the gel supporting surface is curved slightly to conform to the curvature of the gel.

5. A device as in claim 4 wherein the gel supporting surface further includes side portions of pronounced curvature.

6. A device as claimed in claim 1 wherein the reservoir is located above the gel supporting surface.

7. A device as claimed in claim 6 wherein the reservoir is a single unit whereby cooling liquid is adapted to move without obstruction in the reservoir.

8. A device for use with an electrophoretic gel wherein the gel has first opposite edges defining a first dimension thereof and second opposite edges defining a second dimension thereof, comprising:
   a gel supporting surface;
   members including means adapted to engage the first opposite edges of the gel and hold the gel against the gel supporting surface; and
   the members further including means adapted to engage second edges of the gel and hold the gel against the gel supporting surface and wherein either the first means or the second means is operative at a time.

9. A device selectively and operatively for use with one of a plurality of electrophoretic gels wherein one such gel has opposite edges defining a first dimension and another such gel has opposite edges defining a second dimension, comprising:
   a gel supporting surface;

members including first means adapted to engage the opposite edges of the one such gel and hold the gel against the gel supporting surface;

the members including second means adapted to engage opposite edges of the another such gel and hold the gel against the gel supporting surface and wherein either the first means or the second means is operative at a time;

a liquid holding reservoir and the gel supporting surface sharing a wall that is common with the reservoir; and a cover adapted to close the reservoir including valve means for venting the reservoir when the cover is in a first orientation and for closing when the cover is in a second orientation.

10. A device as in claim 9 wherein the gel supporting surface is curved slightly to conform to the curvature of the gel.

11. A device as in claim 10 wherein the gel supporting surface further includes side portions of pronounced curvature.

12. A device for use with an electrophoretic gel wherein the gel has first opposite edges defining a first dimension thereof and second opposite edges defining a second dimension thereof, comprising:

a gel supporting surface;

members including first means adapted to engage the first opposite edges of the gel and hold the gel against the gel supporting surface;

the members further including second means adapted to engage second edges of the gel and hold the gel against the gel supporting surface and wherein either the first means or the second means is operative at a time;

a liquid holding reservoir and the gel supporting surface sharing a wall that is common with the reservoir; and a cover adapted to close the reservoir and the cover including valve means for venting the reservoir when the cover is in a first orientation and for closing when the cover is in a second orientation.

13. A device as claimed in claim 12 wherein the gel supporting surface is curved slightly to conform to the curvature of the gel.

14. A device as claimed in claim 13 wherein the gel supporting surface further includes side portions of pronounced curvature.

15. A device for use with an electrophoretic gel comprising:

a gel supporting surface wherein the gel has opposite edges, comprising:

members including means adapted to engage the opposite edges of the gel and hold the gel against the gel supporting surface; and a liquid holding reservoir and the gel supporting surface shares a wall that is common with the reservoir; and a cover adapted to close the reservoir and the cover includes valve means for venting the reservoir when the cover is in a first orientation and for closing when the cover is in a second orientation.

16. A device as in claim 15 wherein the gel supporting surface is curved slightly to conform to the curvature of the gel.

17. A device as in claim 16 wherein the gel supporting surface further includes side portions of pronounced curvature.

* * * * *

UNITED STATES PATENT AND TRADEMARK OFFICE
CERTIFICATE OF CORRECTION

PATENT NO. : 4,865,714

DATED : September 12, 1989

INVENTOR(S) : Sohn, et al.

It is certified that error appears in the above-identified patent and that said Letters Patent is hereby corrected as shown below:

Claim 1, line 22, "members first" should read "members including first"

Signed and Sealed this

Thirteenth Day of November, 1990

Attest:

HARRY F. MANBECK, JR.

*Attesting Officer*     *Commissioner of Patents and Trademarks*